United States Patent [19]

Rubin

[11] Patent Number: 4,854,323
[45] Date of Patent: Aug. 8, 1989

[54] ELECTROCARDIOGRAPH HARNESS

[76] Inventor: Lawrence A. Rubin, 58-29 155th St., Flushing, N.Y. 11355

[21] Appl. No.: 201,552

[22] Filed: Jun. 2, 1988

[51] Int. Cl.[4] .............................................. A61B 5/04
[52] U.S. Cl. .................................................. 128/644
[58] Field of Search ............................... 128/639–641, 128/643, 644, 783, 791–793, 798, 799, 802, 803, 380, 384, 358

[56] References Cited

U.S. PATENT DOCUMENTS

| 3,709,228 | 1/1973 | Barker | 128/791 |
| 4,082,086 | 4/1978 | Page et al. | 128/640 |
| 4,207,904 | 6/1980 | Greene | 128/798 |
| 4,233,987 | 11/1980 | Feingold | 128/639 |
| 4,328,814 | 5/1982 | Arkans | 128/640 |
| 4,353,372 | 10/1982 | Ayer | 128/640 |
| 4,432,367 | 2/1984 | Piesinger | 128/639 |
| 4,573,474 | 3/1986 | Scibetta | 128/644 |
| 4,583,549 | 4/1986 | Manoli | 128/640 |
| 4,608,987 | 9/1986 | Mills | 128/639 |

FOREIGN PATENT DOCUMENTS 0206070  1/1984  Fed. Rep. of Germany ...... 128/644

Primary Examiner—Lee S. Cohen
Attorney, Agent, or Firm—Andrew S. Langsam

[57] ABSTRACT

An electrode harness for an electrocardiograph apparatus has a hollow tube for containing and housing the individual lead wires for each electrode and a flexible stylet which when bent, into a desired shape, will maintain that shape, until reshaped. The individual electrodes are slidably adjustable about the exterior of the hollow tube to enhance precise positioning of the electrodes to thereby maximize the proper recording of electro-cardiac information from the patient. All of the individual lead wires are bundled together and exit from the hollow tube at a single location. In addition, the electrical plug for the harness is uniquely configured so that it can only be plugged into the corresponding female receptacle of the electrocardiograph recording machine in the proper manner. The harness is also provided with a pair of straps which are adapted to be placed beneath the right shoulder and the left hip of the patient. The weight of the tube and/or stylet also provides a downward bias of the harness towards the skin surface of the patient to maximize electrical contact between electrodes and patient.

13 Claims, 2 Drawing Sheets

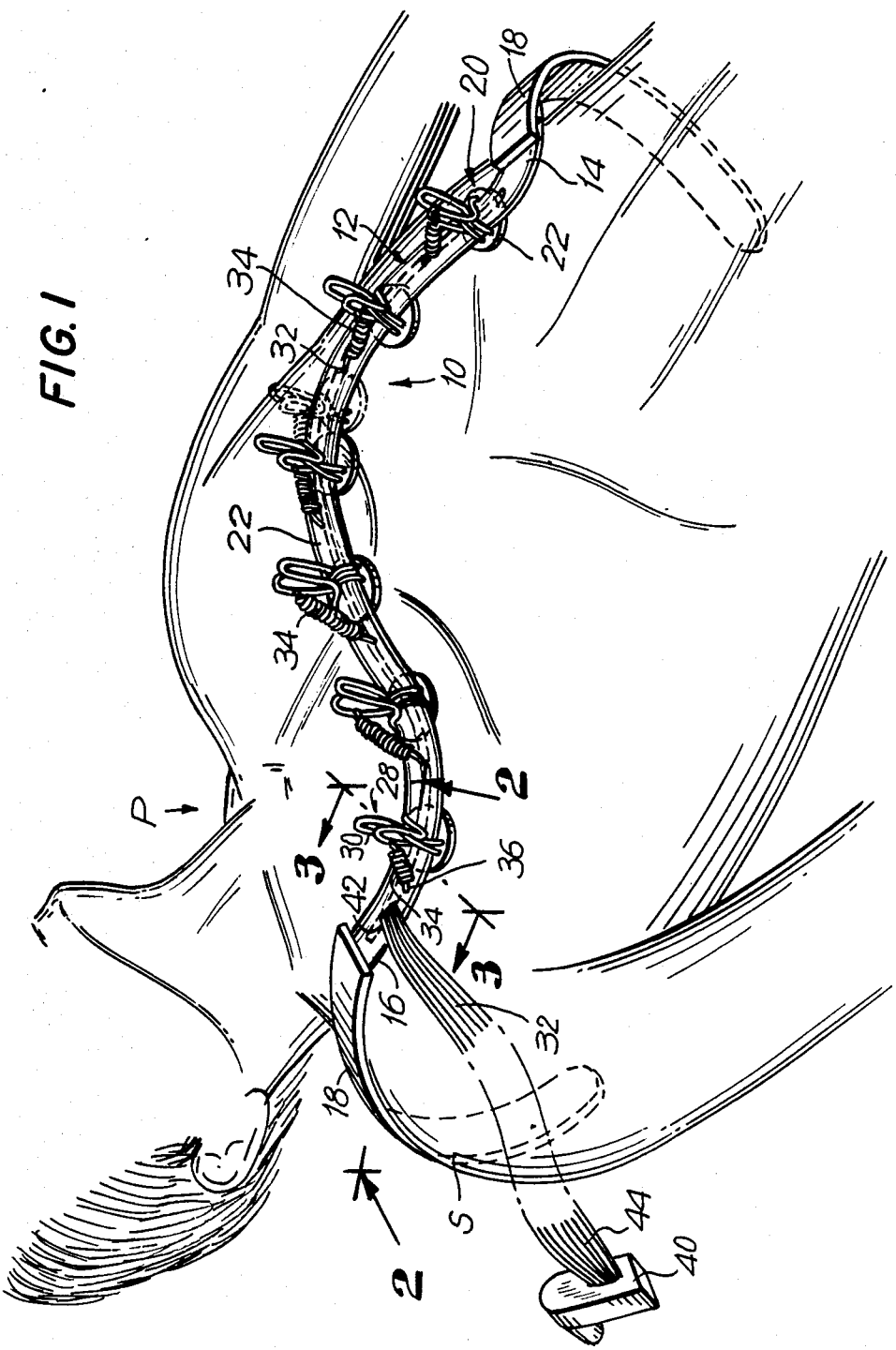

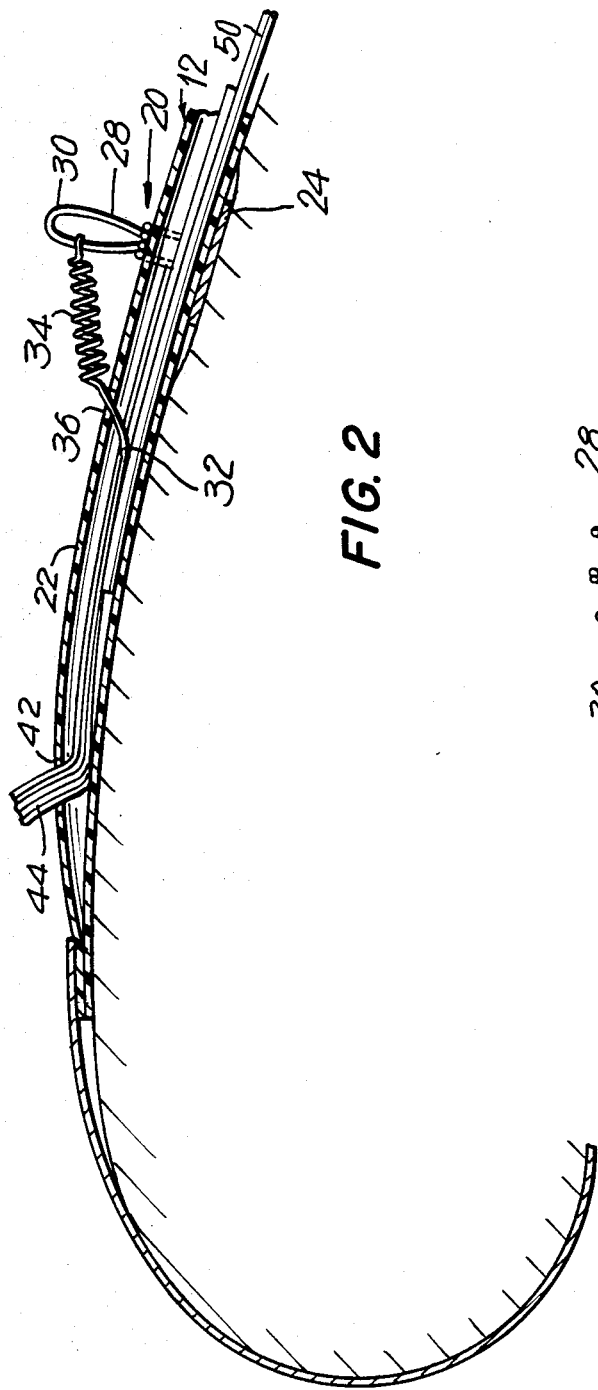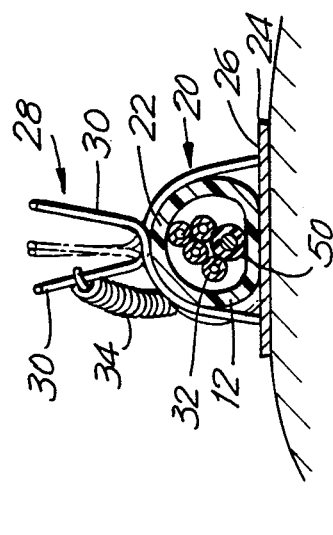

ELECTROCARDIOGRAPH HARNESS

BACKGROUND OF THE INVENTION AND DESCRIPTION OF THE PRIOR ART

The present invention relates, generally, to the field of electrocardiography. Specifically, the present invention relates to an electrocardiograph harness carrying a multiple of electrodes which when electrically connected to an electrocardiograph recording apparatus receive, transmit and record valuable electrical information about a patient's health and, in particular, the health and condition of the patient's heart.

Electrocardiograph harnesses are now available which carry the required number of electrodes for chest area and limbs. They suffer, however, from various disadvantages. For example, the prior art harnesses are incapable of being easily adapted to both large adults and then to small children. Rather, however, the prior art harnesses are provided in different sizes and the size of the patient dictates the selected size of the harness. This, however, in an emergency room environment, where time is critical, can clearly cause problems. The present invention enables the doctor or technician to quickly and accurately "grossly" mold the harness to the size and shape of the patient and then to "fine tune" the location of the electrodes on the harness since they are slidably adjustable.

The electrodes of the prior art are generally attached and held to the patient's body by either suction cups and/or an electrolytic gel or paste which both establish good electrical and adhesive contact between the electrodes and the patient's skin. However, it is quite frequent that the suction, over time, of the electrodes diminishes to the point where the electrodes fall off of the patient and/or the gel or paste losses its adhesiveness such that the electrodes become detached from the patient. Again, in an emergency room situation, this is highly undesirable. Even in a doctor's office, the recording of the health and strength of the heart is a very high anxiety producing medical procedure, which anxiety is raised when the patient recognizes that the electrodes have become disengaged from his or her body. The present electrode harness, as will be more fully explained hereinafter, firmly secures the electrodes to the patient's skin by enhancing the otherwise available attachment by suction and/or electrolytic paste or gel with the downwardly biased weight of an electrode-carrying tube, containing the electrode lead wires and the weight of a contained stylet. This further ensures that the electrodes will be maintained in place.

Multiple electrodes are also available for use with an electrocardiograph recording apparatus where the individual electrodes are connected, by rather long lead wires to a central electrical signal distribution box-like structure. The technician who is charged with the responsibility of readying the patient for the cardiac recording procedure is expected to quickly and accurately attach each electrode, in a particular order, to the patient, in a minimum of time. Because of the time pressure, again in medical emergency situations where a heart attack or stroke is a possibility, or even in the doctor's office, during a routine medical check up, where the technician is inattentive, the electrodes can quite easily be accidentally switched in order and a false and misleading recording of the patient's health and heart condition can result. Clearly, this, too, is highly undesirable. The present invention, in contrast, prelocates the individual electrodes, in the proper order for recording, in their approximate, desired location so that false readings and recordings are eliminated. Adjacent electrodes, connected to the recording apparatus, can no longer be accidentally switched in position. Also, the electrical plug which connects the harness and the individual electrodes to the recording apparatus is uniquely shaped so that it can only be plugged into the recording apparatus in a precise manner to result in accurate "tracings" or recordings.

Basically, the general concept of the present invention relates to an apparatus for simply, quickly and efficiently readying a patient for an electrocardiograph test procedure. The apparatus is intended to be electrically connected to an existing electrocardiograph recording machine. The lead wires for the electrodes, which are normally individually wired back to the recording apparatus, are passed through a hollow conduit which eliminates the possibility of accidental switching of the order of the electrodes. Furthermore, the conduit which carries the wires for the electrodes also carries a flexible metal-like rod (a stylet) which can be repeatedly bent to a size and shape for a particular patient, will hold the newly formed shape and, yet, can be rebent to a new size and shape for a different patient. This allows the apparatus to be used over and over again, and, yet, gives the technician the ability to simply and quickly form or shape the hollow conduit to the particular physical characteristics of the patient. Also, the weight of the stylet, contained within the conduit, enhances the tendency of the electrodes, carried by the conduit, to be weighted or downwardly biased towards the patient's skin for superior electrical contact.

It is another aspect of the present invention for the individual electrodes to be longitudinally adjustably slidable along the length of the conduit while, however, always remaining electrically connected to the recording apparatus. This, too, gives the technician flexibility in adapting, molding, shaping, etc., the device to the physical size, shape, location of heart, etc., characteristics of the patient. This aspect of the invention is accomplished by the use of spring-like clips attached to the electrodes. When the ears of the clips are squeezed together, the electrodes are capable of being horizontally adjusted along the length of the tube and when the ears of the clips are released, the electrodes will be precisely located along the length of the conduit.

The following prior art was uncovered and reviewed pursuant to a preliminary patentability search.

| U.S. Pat. No. | Date | Inventor |
| --- | --- | --- |
| 4,608,987 | 09/02/86 | Mills |
| 4,583,549 | 04/22/86 | Manoli |
| 4,573,474 | 03/04/86 | Scibetta |
| 4,353,382 | 10/12/82 | Ayer |
| 4,328,814 | 05/11/82 | Arkans |
| 4,233,987 | 11/18/80 | Feingold |

The Arkans reference appears to be the closest teaching uncovered in the search. It shows an ECG strip with a plurality of electrodes attached thereto. The wiring for the electrodes are held together to avoid entangling with one another. The electrodes are somewhat horizontally adjustable along the strip and the electrodes' wires terminate at a single common electrical male member. However, there is no teaching of a flexible stylet housed in the conduit which contains the individual electrical leads for the electrodes, the stylet providing both weighting of the electrodes onto the patient's skin and, in addition, allowing the harness to be "molded" and shaped to the patient's chest size and shape. The stylet enables the tube or conduit of the harness to be grossly shaped, as desired. The stylet holds that shape until molded again for use on another patient. Also, the spring clips which are used for precisely locating and adjusting the electrodes are far easier and more "sure to the touch" than the manner of doing the same as shown in the Arkans device. Release of the ears of the spring clips, after placement of the electrodes, ensures no further movement of the electrodes, while the electrodes of Arkans can easily move, even after placement.

In addition, the Arkans reference's device does not appear to be able to hold onto perspiring or restless patients, while the present invention, by the simple use of leather straps located below the patient's right shoulder and left hip (left upper quadrant) prevents accidental movement of the electrodes. Also, if electrode gel spills or gets smeared during the diagnostic procedure, it is far easier to clean the same from the plastic tubing of the present invention than it would be to clean the Arkans device. Finally, with respect to Arkans, it does not appear to be useful for pediatric use since the electrodes do not appear to be able to slide close enough together for small chest sizes. Here, again, the present invention is quite flexible and moldable to both large and small patient chest sizes, whether skinny or fat.

The Mills reference relates to an apparatus for transmitting ECG data and comprises a vest-like garment having a plurality of apertures adapted for receiving electrodes. According to the specification of the patent, the individual electrodes are downwardly biased against the front panel of the vest and towards the skin surface of the patient to provide better electrical contact. The specification further provides that it is an additional feature of the invention to have each electrode in a fixed position relative to other electrodes. There is neither a teaching nor a suggestion of using a hollow conduit containing the individual electrode lead lines (which decreases patient anxiety and avoids entanglement between the leads) nor of having a shapable stylet contained therein for molding the harness to individual patient's chest size and shape, thereby resulting in an apparatus which efficiently and precisely places and locates multiple electrodes, thereby eliminating the possibility of switching one electrode for another. The Mills reference really does not teach a means for ensuring that electrodes and their "leads" do not become switched and, in addition, the electrodes are not adjustably held by the vest (in contrast to the present invention's horizontally adjustable electrodes) but, rather, the electrodes of Mills merely pass through apertures of the vest and are connected to the electrical leads. The downward biasing of the device in Mills is accomplished by a compression providing member (a spring) and not a moldable stylet. The stylet of the present invention, however, also allows the harness to be grossly molded to the patient's physique. Fine adjustment of the electrodes is accomplished by sliding them on the length of the tube. Finally, Mills's device is a closed vest, which is more constraining and anxiety producing than a simple conduit overlying the patient's chest and, again, in emergency medical situations, it is far easier to "fit" the patient with the harness than to clothe a patient with a vest.

The Manoli device relates to an ECG electrode pad made from flexible non-conductive material with a plurality of electodes fixedly placed thereon. Again, in contrast, the present harness allows for precise adjustment of the electrodes by the spring clips. Manoli and Mills state that three sizes of their devices should be capable of handling most sized patients. Contrarily, one harness of the present invention can handle most sized patients. Thus, the present device can eliminate the requirement for a plurality of devices to be readily available. Also, the Manoli device has little flexibility to conform to truly different shapes since the pad has the wiring etched thereon and the pad is not capable of significant molding or shaping.

The Scibetta reference relates to a cable harness for an ECG device. Its primary purpose and function is to enable monitoring of heart activity and, yet, when required, the entire central portion, with its electrodes, can be simply removed, in an instant, to allow heart massage, if required. The "booms" of the device, through which the electrodes pass, are not flexible and, therefore, do not truly provide the degree of flexibility and ability to mold to the patient's size and shape, which the hollow tube with stylet contained therein provides. Also, the present harness device is much more "open" and less anxiety producing to a patient since it is less constraining. The Scibetta reference does, however, seem to show a plurality of electrodes exiting through a boom arm with the wiring internally confined within the arm. There is no teaching, however, of having the arm, itself, provide any downward biasing or weight to enhance electrode contact with the patient's skin and, indeed, the use of suspended arms over the patient's chest area teaches away from the direct downward pressure which the stylet contained within a tube having electrode lead wires provides.

The Ayer reference is for a medical cable set and electrodes. There is no teaching of a flexible, weight-providing stylet contained within the harness's tube nor of having a moldable stylet for gross shaping to the patient's size and shape. Also, the spring clips of the present invention give unique fine location of the electrodes and, once located, fixedly hold them in place. The electrodes of Ayer can be first positioned but, then, can easily shift on the patient since they are not, in any way, held or constrained in place. Ayer does, however, show a common male plug member for plugging into the ECG recorder, but it is symmetrically shaped and, therefore, it can accidentally be flipped over to be plugged into the recorder with the electrodes thus providing incorrect information. The uniquely shaped male plug member of the present invention is designed to only be able to be inserted into the female receptacle in but one manner, thereby precluding inaccurate connection between an electrode and the recording instrument, which could then be interpreted by the doctor or technician, with potentially disastrous results.

The Feingold reference is quite similar to the pad shown in the Manoli patent but, here, the pad can be selectively torn to provide a little more flexibility in electrode placement. It is far easier to use the present invention's spring-like clips to place the electrodes accurately than it appears it would be for the technician to rip the pad and then place the electrodes of Feingold. The ease of use of the present harness is clearly superior to that shown in Feingold. Also, the present invention can be repeatedly used on patient after patient, whereas a ripping of Feingold renders the device inapplicable to a different size or shape patient.

SUMMARY OF THE INVENTION

The electrocardiograph harness basically comprises a hollow tube which is adapted to contain all of the electrode lead wires. The wires are, of course, electrically connected to the individual electrodes. The electrodes, serving as receptors for the electrical stimulii of the patient's heart are slidably maintained on the hollow tube with the lead wires exiting, and connecting to the electrodes, from the hollow tube, at or about the position of the electrodes. A metal-like stylet is also contained within the hollow tube and facilitates the quick, on the patient, bending and shaping of the harness to the size and shape of the patient. The stylet is flexible so that it can easily be bent, as desired, and, yet, after bending, it will hold its shape until bent again. The stylet is sufficiently sturdy so that it can be repeatedly bent and rebent without breaking and, thus, is capable of being used on patient after patient. The bendability of the stylet, housed within the hollow tube, of course, causes the flexible hollow tube to assume the same shape as the stylet. This allows the harness to be used by a wide range of patient sizes, including small children and large adults, whether skinny or fat. As an alternate embodiment of the present invention, the hollow tube, housing the electrode lead wires, can be, itself, made from a material which can be repeatedly bent and, once bent, will maintain the shape until rebent.

The ends of the harness are provided with leather-like straps which are adapted to be easily and comfortably located below the patient's right shoulder and left hip. This establishes an initial basic configuration for the harness which can then be further shaped to the precise patient mesomorph, i.e., body size and shape, so that the electrodes are positioned proximal to the proper body areas for accurate recording. Then, to further "fine" locate the electrodes, they are individually slidable along the outside of the hollow tube and, once located, they will be maintained in relative position by manual release of spring clips (the ears of the spring clips having been manually grasped and pushed together to enable ease of movement of the electrodes along the hollow tube). The lead wires, housed within the hollow tube, as mentioned, individually exit the tube proximal to an average location of the desired electrode placement on a patient. The lead wires are connected to the electrodes with a coil of wire adjacent to the electrodes. This allows for the electrode to be moved along the tube without unnecessary lengths of wire being exposed and thereby looking sloppy.

All of the electrode lead wires exit from the hollow tube, as a bundle, proximal to the desired location of the electrocardiograph recording apparatus. The wire bundle terminates in a uniquely shaped male electrical plug which is adapted to be inserted into a corresponding female receptacle of the electrocardiograph recording apparatus. In this manner, the individual electrodes can only be electrically connected to the recording apparatus in the proper order and false recordings or readings of the patient's health and heart condition are entirely eliminated.

BRIEF DESCRIPTION OF THE DRAWINGS

FIG. 1 is a perspective view of the electrocardiograph harness of the present invention, in position on a lying-down patient (shown partially) and prior to electrical attachment of the harness to the electrocardiograph recording apparatus;

FIG. 2 is a cross-sectional view of the harness, taken along lines 2—2 of FIG. 1; and FIG. 3 is a cross-sectional view of the harness and an electrode, taken along lines 3—3 of FIG. 1.

DETAILED DESCRIPTION OF THE INVENTION AND THE PREFERRED EMBODIMENT

As best seen in FIG. 1, an electrocardiograph harness 10 basically comprises a flexible otherwise hollow tube 12, having a leather strap 18 attached on its two ends 14 and 16. The tube can have a flattened bottom to facilitate location and maintenance on the patient's chest. According to the current preferred embodiment of the present invention, the ends 14 and 16 of the hollow tube 12 are slit, about 2 to 3 inches in length, so that the straps 18 can be stapled or otherwise conventionally secured to the now-flattened ends of the tube 12. With a patient P lying on the doctor's examination table, the first thin leather strap 18 can easily be inserted or placed between the patient's right shoulder S and the operating or examination table and, in addition, the other leather strap 18 is inserted between the patient's left hip and the examination table. This serves to basically hold the harness is place.

A set of electrodes 20, generally six for the patient's chest area, are secured around the exterior circumference 22 of the tube 12. Each electrode 20 has a thin, metallic, circularly-shaped disc element 24 which is intended to directly contact the patient's skin or, if preferred, an electrolytic gel or paste can be used to ensure electrical and physical contact between the disc element 24 and the patient's skin. Alternatively, the electrodes 20 can be of the currently available suction cup type to further enhance the attachment and securement of the electrodes to the patient. As best seen in FIG. 2, the rear or top surface 26 of the disc element 24 is provided with a spring clip 28 having a pair of upwardly extending ears 30, which encircle the tube 12. Grasping the two ears 30 of the clip 28 of a particular electrode 20, and causing the ears of the clip to approach one another, releases the frictional engagement between the spring clip and the exterior circumference of the tube 12 so that the electrode can easily be slid, a short distance, along the length of the tube 12. When the electrode 20 is precisely located, where desired, the ears 30 are manually released and the spring action of the ears of the clips 28 causes the reengagement and frictional securing of the electrodes 20 about the exterior circumference of the tube 12. This, then, ensures precise location of the individual electrodes, in strict conformity with the patient's chest size and shape, and the location of the patient's heart.

Each electrode 20 is electrically connected to a lead wire 32. A coiled portion 34 of the lead wires 32 is located immediately adjacent to the electrode 20. Ultimately, through a suitable electrical connection, the electrodes are connected to an electrocardiograph recording apparatus (not shown). The coiled portion 34 of the lead wires 32 allows for precise movement and location of each electrode, while always maintaining electrical contact between the electrode and the lead wire. The coiled portion 34 ensures that readily available additional wire is present for the electrode, if it is moved far away from the opening 36 for the lead wire 32 and, yet, when the electrode's ultimate desired location is near to its corresponding opening 36, the excess wire is visually attractive and functionally, out of the way, so as not to interfere with the examination procedure (listening through a stethoscope, immediate access for heart massage or an injection, for examples). The recording apparatus is not a part of the present invention and available prior art devices, if either originally manufactured with the female electrical receptacle to be herein described or existing machines, retrofitted with the specially configured female receptacle, can be employed.

The individual lead wires 32 pass through corresponding openings 36 of the tube 12, located behind the coiled portion 34, and the individual leads are bundled together within the hollow interior of the tube 12, as the wires 32 come into contact with the other lead wires within the tube of the harness. Clearly, the lead wire 32 for the electrode 20 which is farthest away from the electrical male plug member 40, is longest in length, while the lead wire 32 for the electrode located nearest to the electrical male plug member 40 is shortest in length. As the lead wires pass, within the tube 12, the lead wires of adjacent electrodes are bundled together. A single bundle opening 42 is cut into the tube 12 and serves as the point of exit for the entire bundle of wire 44, including all lead wires 32, from the interior of the tube 12. The bundle of wire 44 is then electrically secured and attached to an electrical male plug member 40.

The electrical male plug member 40 is uniquely configured and adapted to be plugged into a correspondingly configured electrical female receptacle member (not shown) in but one manner, so that the electrical lead wires for the electrodes are necessarily connected to the electrocardiograph recording apparatus in only one way and, therefore, accidental attachment of the leads in the wrong order is avoided as is the otherwise expected inaccurate diagnostic results. In addition, it should be appreciated that the relative location of the individual electrodes on the tube 12, in the orientation and order first established during manufacture, eliminates the accidental switching by the doctor or technician, of one electrode, during placement on the patient, with an adjacent electrode or other electrode. This, too, only enhances the reliability of the diagnostic procedure.

A stylet 50, in the preferred form, a metallic flexible rod, is also housed within the tube 12. The stylet is made from a material which can easily be bent into a preferred shape, will then hold the shape, force and hold the tube in the same shape along with the lead wires 32 contained therein, until the doctor or technician reshapes the harness. The material for the stylet is to be relatively durable so that a large multiple of shapings can occur without breakage. Thus, the present harness can be used by patient after patient, and is expected to last for a long period of time. Preferably, the stylet 50 is a metal wire which is fully insulated from the lead wires by being encased in a rubber coating. Alternatively, the tube 12, itself, can be made from a material which, when bent, will maintain its bent shape, until rebent, and, in addition, the tube can be bent and rebent over and over again for use by many patients.

The stylet 50 allows the tube 12 to be quickly molded and shaped by the doctor or technician to conform to the patient's size and shape to provide a gross approximation of the electrode placement for an accurate electrocardiograph procedure. This gross shaping can be established, either before or after the leather straps 18 are located, as described above. Then, the individual electrodes 20 are slid along the exterior circumference or surface of the tube 12, until precisely located. This, then, is the "fine" adjustment, again, to ensure a technically precise electrocardiograph diagnostic procedure. The apparatus can be quickly removed from the patient, if required, in that it is not a vest-like device.

In addition, the weight of the stylet 50 further enhances the downward bias or weighting of the harness on the patient. This further establishes electrode contact with the patient, again, leading to better medical diagnosis. Alternatively, the tube 12 can be weighted to facilitate the bias of the electrodes against the patient's skin for superior electrical contact.

It should be understood, of course, that the specific form of the invention herein illustrated and described is intended to be representative only, as certain changes may be made therein without departing from the clear teachings of the disclosure. Accordingly, reference should be made to the following appended claims in determining the full scope of the invention.

I claim:

1. An electrocardiograph harness comprising a fully flexible tube capable of being shaped by hand and having at least one electrode secured thereto, a lead wire electrically attached to each of said at least one electrode, and a flexible tube shaping and shape retaining means for allowing a repeated selective bending of said tube by a shaper's hands into a desired shape and holding said desired shape even after removal of the shaper's hands until a following bending into a new desired shape.

2. An electrocardiograph harness as claimed in claim 1, wherein said at least one electrode is provided with electrode adjustment means for slidably adjusting said at least one electrode along the length of said tube.

3. An electrocardiograph harness as claimed in claim 2, wherein said electrode adjustment means comprises a spring-like clip secured to each at least one electrode and, in its normal position, frictionally engaging the exterior of said tube, while in its adjustable position, being released from said frictional engagement.

4. An electrocardiograph harness as claimed in claim 2, further comprising a coiled portion of said lead wire adjacent to each of said at least one electrode.

5. An electrocardiograph harness as claimed in claim 1, wherein said tube shaping and shape retaining means comprises a metallic stylet contained within said tube.

6. An electrocardiograph harness as claimed in claim 5, wherein said metallic stylet is coated with rubber.

7. An electrocardiograph harness as claimed in claim 1, wherein said tube shaping and shape retaining means is said tube, itself.

8. An electrocardiograph harness as claimed in claim 1, further comprising a pair of straps, one strap located at each of the ends of said tube for location beneath both the shoulder and hip of a patient during use of said harness.

9. An electrocardiograph harness as claimed in claim 1, wherein each of said lead wires are substantially housed in said tube.

10. An electrocardiograph harness as claimed in claim 1, wherein each of said lead wires are bundled together and exit said tube as a single bundle at the ends of said wire leads remote from the ends of said wire leads connected to said at least one electrode.

11. An electrocardiograph harness as claimed in claim 1, wherein said tube shaping and shape retaining means downwardly biases each of said at least one electrode into electrical contact with a patient wearing said harness.

12. An electrocardiograph harness as claimed in claim 1, wherein the weight of said tube downwardly biases each of said at least one electrode into electrical contact with a patient wearing said harness.

13. An electrocardiograph harness as claimed in claim 1, wherein the bottom surface of said tube is slightly flattened to facilitate maintenance of said harness in position.

* * * * *